United States Patent
Chalmers et al.

(10) Patent No.: US 7,641,916 B2
(45) Date of Patent: Jan. 5, 2010

(54) DIGESTIBLE AND VOLUME ADJUSTABLE MULTI MEDICATION DELIVERY DEVICE

(75) Inventors: Anne Marie Chalmers, Osprey, FL (US); Bo Martinsen, Osprey, FL (US)

(73) Assignee: Ambo Innovations, LLC, Osprey, FL (US)

( * ) Notice: Subject to any disclaimer, the term of this patent is extended or adjusted under 35 U.S.C. 154(b) by 395 days.

(21) Appl. No.: 11/407,680

(22) Filed: Apr. 20, 2006

(65) Prior Publication Data

US 2006/0254580 A1 Nov. 16, 2006

Related U.S. Application Data

(63) Continuation of application No. PCT/US2004/035178, filed on Oct. 21, 2004.

(60) Provisional application No. 60/613,804, filed on Sep. 28, 2004.

(51) Int. Cl.
*A61K 9/48* (2006.01)
*A61K 9/64* (2006.01)

(52) U.S. Cl. .............. 424/451; 451/453; 451/456

(58) Field of Classification Search ............... None
See application file for complete search history.

(56) References Cited

U.S. PATENT DOCUMENTS 4,936,461 A * 6/1990 Makiej, Jr. ................ 206/528
5,182,111 A * 1/1993 Aebischer et al. ........... 424/424
5,558,878 A 9/1996 Paulos
5,672,359 A * 9/1997 Digenis et al. .............. 424/463
5,916,584 A 6/1999 O'Donoghue et al.
6,350,468 B1 * 2/2002 Sanso ...................... 424/456
6,543,692 B1 4/2003 Nellhaus et al.
7,294,346 B2 11/2007 Chalmers
2003/0108705 A1 6/2003 Duffield et al.
2005/0008690 A1 * 1/2005 Miller ...................... 424/451

FOREIGN PATENT DOCUMENTS

EP        0308637 A1    3/1989
WO    WO-02/45618 A2    6/2002

OTHER PUBLICATIONS

International Search Report for Application No. PCT/US2004/035178, dated Feb. 24, 2005.

* cited by examiner

*Primary Examiner*—S. Tran
(74) *Attorney, Agent, or Firm*—Lahive & Cockfield, LLP; Jane E. Remillard; Brian C. Trinque

(57) ABSTRACT

A volume-adjustable device for the delivery of multiple medications to a subject, the device comprising multiple medication elements; an outer containment means having at least one open end into which the medication elements are removeably inserted; and a closure means removeably and adjustably inserted into at least one end of the outer containment means is disclosed.

27 Claims, 7 Drawing Sheets

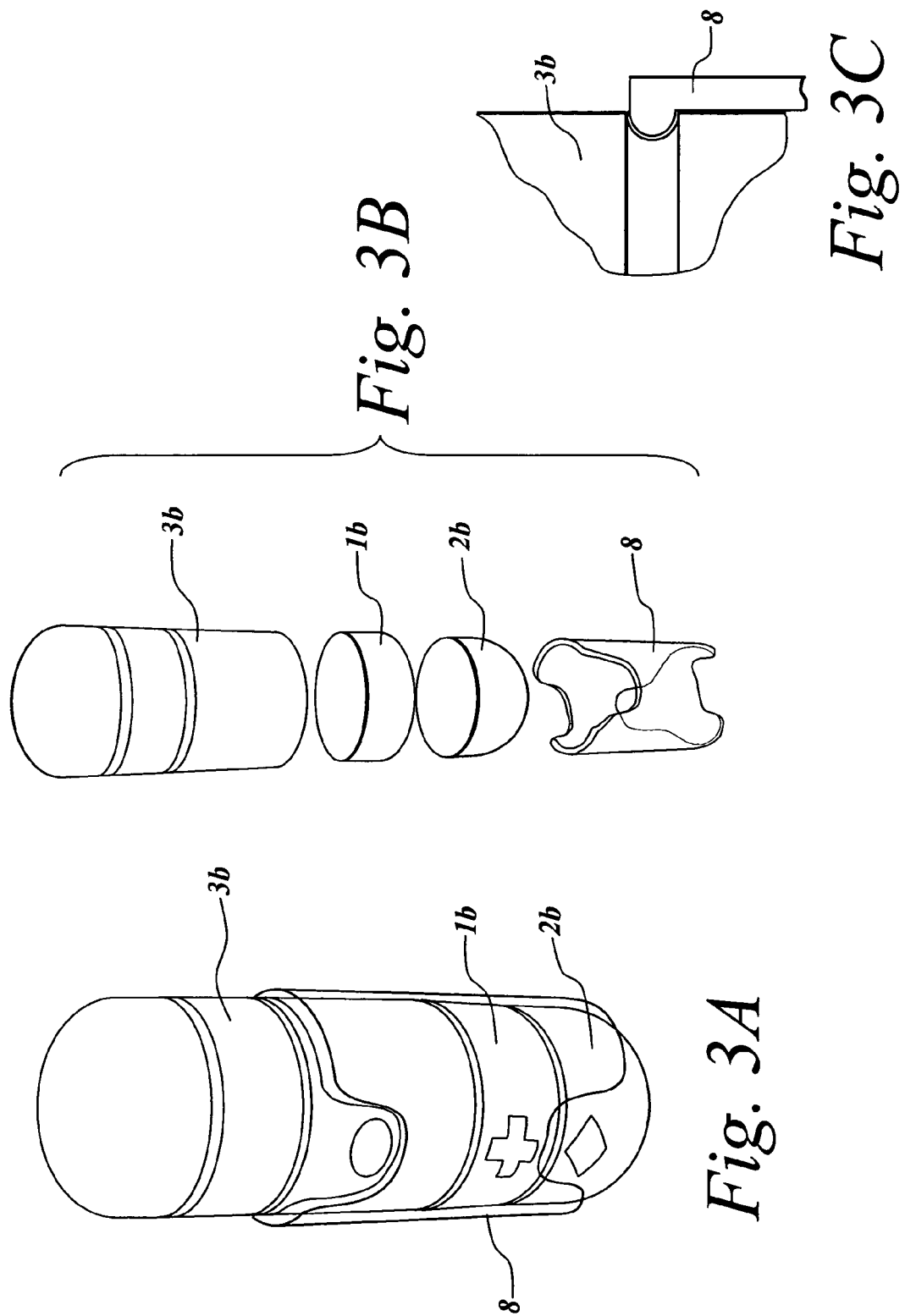

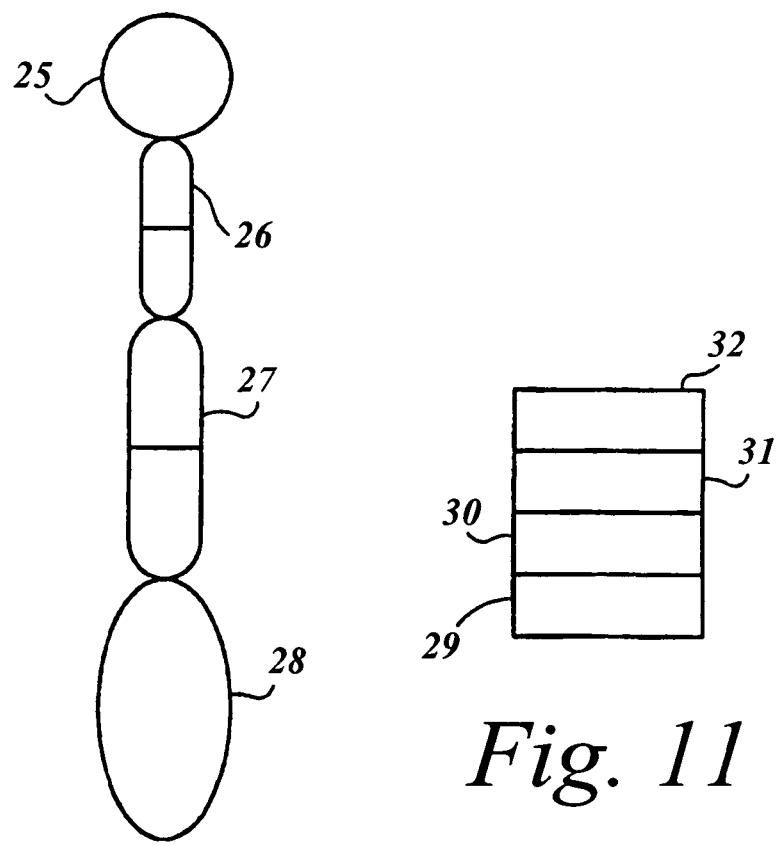
Fig. 10
Fig. 11
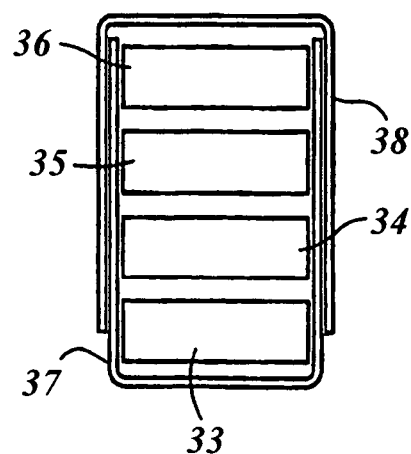
Fig. 12

DIGESTIBLE AND VOLUME ADJUSTABLE MULTI MEDICATION DELIVERY DEVICE

RELATED APPLICATIONS

This patent application is a continuation International Application No. PCT/US2004/035178, filed Oct. 21, 2004, which claims the benefit of Provisional Application No. 60/613,804, entitled "Digestible and Volume Adjustable Delivery Device," filed Sep. 28, 2004, which is incorporated herein by reference in its entirety. International Application No. PCT/US2004/035178 is also a continuation-in part of U.S. Application Ser. No. 10/690,387, entitled "Medication Delivery Device," filed Oct. 21, 2003; and is also a continuation-in part of U.S. Application Ser. No. 10/785,903, entitled "Medication Delivery Device," filed Feb. 24, 2004; and is also a continuation-in part of U.S. Application Ser. No. 10/787,278, entitled "Medication Delivery Device," filed Feb. 26, 2004; all of which are incorporated herein by reference in their entirety.

BACKGROUND OF THE INVENTION

This invention relates to digestible and volume adjustable container devices and multi-medication combination systems that can be used to hold (stack) and ingest simultaneously or sequentially multiple medication products, pharmaceuticals, nutritional products and inert materials.

Through their structure, the delivery devices have the ability to organize a patient's multiple medications into a reduced number of containers. The medication delivery devices are not limited by medication content, type (capsule, tablet, soft gel) or form. The content of these medication delivery systems are easily visually recognizable by the physician or patient. Additionally, the volume adjustable containers can be size adjusted to content or swallowability by both the manufacturer and the consumer. Also, they can be easily opened by the user if so desired.

As used herein, "pill" means any mechanism or means for delivery of medication products or elements to a live body, including, but not necessarily limited to, tablets, capsules, gel caps or soft-gels.

As used herein, "medication product" includes and encompasses, but is not limited to, prescription drugs, non-prescription drugs, over-the-counter drugs, nutritional supplements and inert "filler" materials used in conjunction with any of the foregoing.

As used herein, the words "container" and "containment means" include and encompass not only the traditional medication tablet, capsule, pill, gel cap, soft-gel, suppositories, skin patches and sublingual applications, but also includes and encompasses any and all other medication delivery mechanisms and means and are not synonyms for a "capsule".

As used herein, the words "outer container" means the container or containment means which contains multiple medication products (also referred to herein as "medication elements") as tablets, pills, capsules, soft gels, or liquids, but which itself is not connected with or affixed to another (except in the case where the outer container is connected or fitted with another container means, such as a plug, or further container or containment device in chain, train or string fashion), and which is not itself sequentially imbedded within another container, and which said non-connected and non-affixed container or containment means can be ingested or inserted into a live body. This outer container can itself be made from medication products and is biodegradable.

As used herein, the term "volume adjustable" refers to the ability to reversibly adjust the volume or number of medication elements contained within the medication delivery device. The term "volume adjustable" also refers to the ability to reversibly adjust the overall length or size of the medication delivery device The term "reversibly" means that the volume or size can be increased, then decreased (or decreased then increased) as many times as desired without effecting the integrity of the medication delivery device.

Most medications presently ingested by patients contain significant amount of inert materials or fillers. Parts of these inert materials are often present due to the concentrated nature, and thus small volume, of the actual active ingredient in the medication. If only the active ingredient was presented to a patient, it would often be of a size which was too small for the patient to comfortably handle, resulting in either the patient dropping or losing the medication or the patient ingesting an overdose of the medication.

Many studies show that age and chronic diseases are strongly correlated to the number of prescription medication pills a person is taking. Due to a continually increasingly aging population and increased use of drug therapy, more and more people find themselves taking several (perhaps as many as 4 to 10) pills for treating or preventing illnesses every day. Research has shown that even patients for whom strict adherence to prescribed drug regimens is crucial, rates of non-compliance can still range from as much as 20% to 50% and that this rate increases with the number of pills prescribed.

Each year in the United States, the consequences of poor compliance cost an estimated $100 billion in added health care expenses, lost productivity, and other direct and indirect costs, in addition to personal suffering.

Another consequence of people having to take several pills every day is that the risks of various mistakes are increased. For example, the patient can become confused as to whether they have taken their medications or not. It is then possible that they take too much or too little of their medications; this increases the likelihood that side effects can occur.

It is sadly ironic that the more confused the patient is, the more likely it is that they have even more pills to keep track of and monitor.

According to the United States Food and Drug Administration, 1.5 million Americans were hospitalized in 1978 alone as a consequence of pharmaceutical drugs administered to "cure" them. It was found that some 30% of all hospitalized people suffered further damage from the therapy prescribed to them.

Side effects involving prescription drugs are the fifth leading cause of deaths in the USA.

One means of increasing compliance is to reduce the number of pills (and containers) taken per day, thus reducing patient resistance to swallowing large numbers of pills or the possibility of patients forgetting to take some of their medication, thus reducing the risk of medication-induced error.

Moreover, numerous studies have shown that certain combinations of different substances or medications can dramatically improve the health outcomes through additional or synergic effects. But these combinations most often require the ingestion of more pills which may again lower the compliance.

The delivery of medication products, including prescription drugs, over-the-counter drugs, nutritional supplements and inert materials, has been traditionally accomplished by the use of pills.

Typically, pills are comprised of the active ingredient compounded with inert ingredients for various purposes, including ease of handling small amounts of active ingredients.

When the said mixture of active and inactive ingredients is then compressed to form a tablet, the tablet typically is then coated or covered with a polished "surface" substance functioning as both a physical/chemical barrier and as a helper for smooth swallowing.

Similarly, capsules and soft-gels are composed of an outer material or casing which is dissolved after ingestion by the patient. The interior portion of the capsule or soft-gel is filled with an active ingredient compounded with inert ingredients for various purposes, including ease of handling of small amounts of active ingredients, similar to a pill as described above.

There are several distinctions between capsules vis-à-vis soft gels or gel caps. The major difference between a capsule and a soft gel or gel cap is that a capsule is usually a pre-made two-piece hard shell assembled after the medication filling is prepared, and a soft gel or gel cap is a physically softer gelatin container and made at the same time as the filling of the content. Capsules usually contain solid materials such as powders, although they occasionally do contain liquids, whereas soft gels usually contain oils or liquid, although some soft gels do contain rather powdery substances.

The disadvantage of a typical prescription pill is that it usually contains only one primary medication even when a patient needs several, thus only addressing one type of indication, problem or physiological mode of action.

Another disadvantage of typical prescription pills is that the patient typically has to buy several different pills to cover their medical needs and that the cost of each pill is higher than if the combination was produced by the same manufacturer into one package.

The treatment of many seriously ill or chronic patients requires the use of multiple medications. Many patients find having to take numerous traditional pills burdensome and restrictive, and this causes additional responsibility and worries. Not only is the patient burdened with multiple containers for the various medications, but the patient must also track each pill to assure that they have in fact timely ingested the proper dosage of each such medication.

The need for the patient to recognize each pill is fully understood by the pharmaceutical industry. When a new and patented product enters the marketplace the manufacturer designs the physical appearance of the pill and the container box to brand the medication using unique colors and shapes, being well aware of the fact that after the patent expiration, the patient will resist switching to cheaper and unfamiliar generic versions (with new colors and shapes) as this will require an adjustment of a carefully habituated visual tracking system. In this way a lack of a standardized visual identification system that everybody can understand contributes to making chronic drug therapy more expensive than necessary.

The present invention reflects the fact that:

(1) Most people (up to 70-85%) do not experience any problems swallowing oblong tablets or capsules up to the size of approximately 20-25 mm, although this size is somewhat larger than most of the prescription pills on the market. However, it still means that a substantial number of people would prefer/need smaller sizes to reduce swallowing problems;

(2) Keeping track of one large pill is easier than keeping track of numerous small pills;

(3) Keeping track of one container is easier than keeping track of several;

(4) Many prescription drugs come in pill sizes larger than chemically necessary and the active ingredient is often so minute it needs to be sized up with fillers to become manageable for the consumer, or it needs to fit a specific shape for marketing purposes;

(5) The physician wants to be able to remove or change the dose of particular medications due to the patient response while holding other substances constant;

(6) Combining several medications can increase the therapy effect and reduce side effects;

(7) There are presently no national or international standards for sizes, shapes, colors or visual identification codes for individual pills. Instead, even the same generic component can come in a variety of appearances compared to the brand of the original manufacturer. This makes it confusing and difficult for the patient to switch from one manufacturer to another for the same medication or even for the physician to identify the content of most medication pills or to renew prescriptions in other countries while traveling. It also hinders the development of a basis for automated individualized multi medication prescription fulfillment, where the elements would need to come in some standardized forms. The proposed suggestion of mandatory bar codes on containers by FDA will not solve these problems. Additionally, it is legal to send medications in the mail, even from one country to another. It is a well known problem that this practice gives the opportunity to send illegal substances under the cover of simple capsules. A new visual identification system will lower this risk.

Combining the fact that it is physically possible to add many prescription drugs together into one container, and still maintain an overall volume which is easy to swallow for most people, opens up the possibility of solving the above mentioned compliance problems related to the number of pills and reducing the risk of taking too much or little medication.

Combining the fact that it is physically possible to present multiple medications and combinations into a reduced number of swallowable sized containers, makes it more appealing to patients and physicians to accept the use of multiple and synergistic ingredients to treat or prevent chronic diseases thus increasing drug therapy power.

Combining the fact that it is possible to create a medication container that can hold several medications and can be size adjustable or opened and separated by the patient into individual components, allowing the patient to reduce the size and swallowing problems presented when taking the medications individually, by following the instructions from the physician to remove or change part of the content, will still result in a reduced number of needed container boxes for this patient group and will help the patient to keep all the medications in one place.

An objective of the present invention is to solve the aforesaid problems, including by reducing the number of pills and containers that will contain the originally intended, prescribed or recommended medications and doses, thus increasing compliance and reducing the possibility of confusion, while maintaining the possibility to recognize each medication element and to ingest each medication element sequentially if desired A further objective of the present invention is to create a container system that can hold a variety of substance combinations, shapes or presentations (capsules, tablets, soft gels) without chemical interaction and to present these multiple medication combinations in a reduced number of containers, thereby increasing the patient acceptance of taking multiple medications regularly.

A further objective of the present invention is also to solve the aforementioned problems by facilitating a switch, in certain instances, to relatively less expensive generic products or to combinations of generic and original drugs.

A yet further objective of the present invention is also to enable a world wide visual medication identification system and create a simple, manufacture friendly and general container device for automated patient individualized manufacturing systems/fulfillment centers/pharmacies for multiple medication prescriptions built on international standards for size, shapes, colors, symbols and configuration of pills. This visual identification system can then be translated into traditional bar codes which may be mandatory for packaging in the future.

Previous medication delivery devices known in the art include dividable capsules, dividable tablets and closed capsule systems. However, there is currently no device that allows for combining a tablet with a capsule or soft gel, or that has volume adjustable features for the patient and/or the manufacturer, or that allows for a wide variety of combinations of soft gels, tablets and capsules using as few as two standard outer container elements to efficiently host these combinations. Nor is there currently a device that combines the above mentioned features with visually identifiable different medication elements, or with a medication-containing plug system. Accordingly, improved medication delivery systems would be beneficial in the art.

SUMMARY OF THE INVENTION

The present invention provides a digestible and volume adjustable multi-medication container device and multi-medication combination system by virtue of which multiple medications can be produced in standardized distinctive shapes or in distinctively shaped containers, and/or unit sizes, including differently colored pills which are configured and designed such that they can be inserted into and contained within an ingestible or insertable (e.g., suppository) container which is biodegradable within a live body. These medications are loose, distinct elements that are contiguous with each other and closely fit against each other to minimize void space. Since each such medication element is inside a larger manageable sized outer container it does not need to be handled separately. The need for an excessive inert volume increase becomes unnecessary and thus allows for the manufacturing of the smallest containers possible. This makes it possible to stack even more "pills" inside the outer container before reaching the ingestible size limit. It also assures that the maximum amount of active ingredients of medication is containable within the smallest outer containment means.

Accordingly, the invention provides a means for assembling different forms of medication elements (for example soft gels, capsules and tablets containing different medication substances) into easy to manufacture single digestible unit doses, thus reducing the number of pills to fulfill multi medication prescriptions. The invention further provides a means for achieving this goal using a volume adjustable, separatable device (e.g., that can be easily assembled, unassembled and reassembled in a variety of manners).

The medication delivery device is constructed with multiple components intended to facilitate opening and emptying of its contents, if so desired by the user. The device comprises an outer containment means that is typically comprised of an elongated cup or tube shaped component with the volume of the internal compartment of the containment means being adjustable and variable to accommodate a variety of volumes (e.g., thickness) of the multiple medications, using, for example, a medication plug with undulated surface that can be attached at different intruded positions. The outer containment means is preferably biodegradable within a live body.

The device further comprises a closure means (or "plug") which can be reversibly inserted in whole or in part into the outer containment means to prevent the medication elements within the containment means from falling out. The closure means can easily be removed using an attachment system, for example, consisting of flexible beaks obtained by a split brim and/or a depressible opening at the edge of the open end(s) of the outer containment means.

The active ingredient in each of the medications is not in actual physical contact with the active ingredients of the medication product with which it is contiguously situated within the outer containment means because of the surface barrier between each of them. This surface barrier is preferably colored differently depending on drug category. The outward pointing side of the various juxtaposed containment elements (within the outer containment means) may also be labeled with a symmetric symbol related to a pre established identification code. The symbols of the juxtaposed elements can be arranged in a linear fashion, obtained, for example, using non circular horizontal shapes. In a particular embodiment, one of the medication containers is itself a component of the biodegradable ingestible container and serves as a plug to the outer container.

The several components and elements of the medication delivery device of the invention may be variously constructed of material which is opaque, translucent or transparent.

Accordingly, in one aspect, the present invention provides a volume adjustable device for the delivery of multiple medications to a subject, the device comprising: multiple medication elements, each element having a uniform diameter; an outer containment means having at least one open end into which the medication elements are removeably inserted; and a closure means removeably and adjustably inserted into at least one end of the outer containment means. In one embodiment, the closure means is itself a medication element. In another embodiment, the medication element comprises a soft-gel capsule. In yet another embodiment, the soft-gel capsule contains omega-3 fish oil, multivitamins, minerals, nutraceuticals, over-the-counter medications, prescription medications or inert materials.

In other embodiments of the invention, at least one end of the outer containment means comprises a narrowed orifice with a flexible edge that contacts the closure means. In still another embodiment, the outer container means comprises a hollow tube wherein both ends of the tube are open such that the medication elements or closure means can be removeably inserted or expelled through the ends. In still another embodiment, the outer container means comprises a hollow tube wherein one end of the tube is open so that the medication elements or closure means can be removeably inserted or expelled through the open end, and the other end is closed so that the medication elements or closure means, once inserted, can not be expelled through the closed end. In still another embodiment, at least one open end of the outer containment means has a slit to provide flexibility to the edge of the open end, such that the medication elements or closure means can easily fit through the opening. In yet another embodiment, the outer-containment means is made of transparent material. In yet another embodiment, the outer-containment means is made of biodegradable material. In yet another embodiment, the outer-containment means is made of material formulated with a medication product.

In further embodiments of the invention, the medication product is a nutraceutical. In another embodiment, the multiple medication elements are colored differently according to their content. In another embodiment, the multiple medication elements have distinct symbols on their sides. In yet another embodiment, the multiple medication elements have a non-circular horizontal surface that allows the medication product to be lined up in such a way the distinct symbols are arranged in linear fashion. In yet another embodiment, the closure means has an undulating surface with a number of indentations that the edge of the narrowed orifice of the outer containment means can insert into, such that the medication device has a variable volume depending on the position of the closure means in order to hold medication elements of varying shapes and sizes. In yet another embodiment, the multiple medication elements comprise, respectively, at least one tablet and at least one capsule or soft gel.

Further embodiments of the invention differ from the above mentioned embodiments with respect to the outer container means:

Specifically, in one embodiment, the plug is not necessarily removable from the cup, thus not necessitating any split or flexibility at the brim of the cup. The attachment of the plug to the cup can thus be ensured by friction, glue or snap interlocking means in which respective nodules are mechanically plastically deformable thereby allowing and enabling the nodule on the cup to slide and slip over the nodule or undulation on the plug surface resulting in an affixed assemblage. The inserted elements which contain different medication substances and presentations comprising, for example, at least one tablet and at least one capsule or soft gel, have a diameter allowing them to pass the mechanical fixture means of the cup which can be transparent or not. Another embodiment uses a traditional capsule which is filled with the different loose medication elements and can be transparent or not.

Yet another embodiment does not have any outer container means at all, but uses biodegradable glue on the transformed adjoining surfaces of the size adjusted and "stacked" different medication elements. The glue can vary in hardness allowing for breakage or separation of the individual medication elements at the glue surface or not.

BRIEF DESCRIPTION OF THE DRAWINGS

FIG. 1 shows the same medications in new tablet forms and a new gel cap shape, with each pill being of a particular shape and size, with the diameter of each such pill being uniform and of varying thickness, and being dependent upon the dosage of the medication of which each such pill is comprised.

FIG. 3a is a depiction of assemblage of the new pills into an alternative outer container shaped as a tube with narrowing orifices.

FIG. 3b is an expansion of the assembled medication delivery device of FIG. 3a, showing the individual components.

FIG. 3c is an expansion of the inward pointing beak at the brim of the outer container, interlocking with an indentation in a pill.

FIG. 10 is a depiction of various sized pills (e.g., one tablet, two capsules of different sizes, and a gel cap) connected or affixed to one another in a chain, train or string fashion.

FIG. 11 is a depiction of various pills that have been adjusted to be the same (i.e., uniform) size (i.e., have been "size adjusted"), and stacked and glued together at their adjoining surfaces.

FIG. 12 is a depiction of a traditional capsule filled (maximally packed) with the size adjusted pills shown in FIG. 11.

FIGS. 1 through 12 are not necessarily exhaustive of all embodiments of the invention.

DETAILED DESCRIPTION OF THE INVENTION

A multi medication delivery device and system for efficiently combining different forms of medication presentations, such as capsules, tablets and soft gels, as exemplified by the particular embodiments depicted in FIGS. 1 through 12, provides for the delivery to a living body (e.g., human or animal) of a maximum amount of active ingredients, with a minimum amount of inert materials, of multiple medication products simultaneously or sequentially.

In a particular embodiment, the multi medication delivery device is volume adjustable such that the user can reversibly adjust the size of the device in order to accommodate medication elements of differing numbers and sizes.

In another particular embodiment, the outer casing of the medication delivery device can be made of active ingredients.

Although the more typical method and means for entry into the said living body is by ingestion, the invention also encompasses other forms of such entry, including, but not limited to, suppository form or application to the skin.

Figure 1:
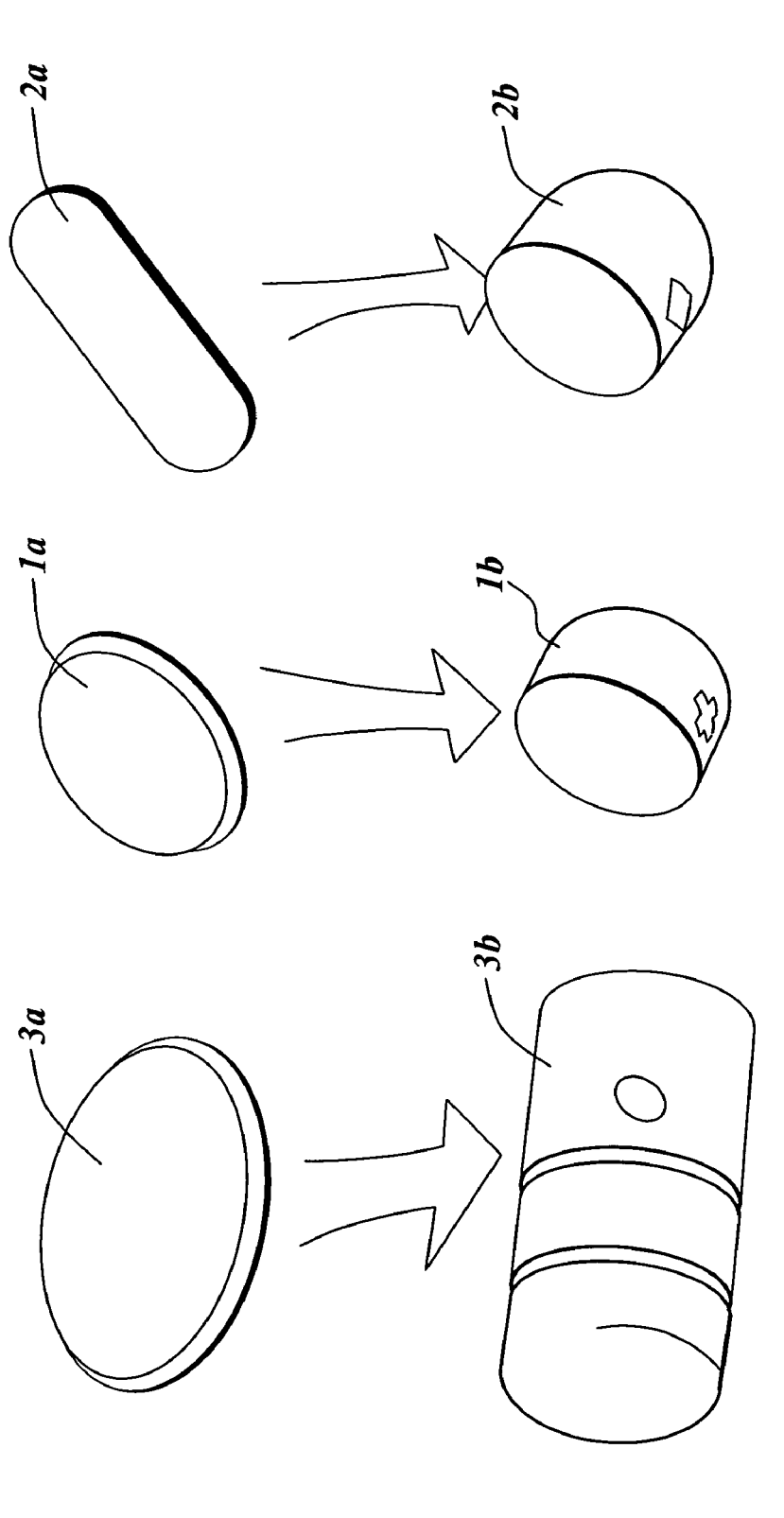
FIG. 1 is a depiction of an assemblage of different medication elements (pills), depicted for illustration purposes as one tablet, one capsule and a soft gel of different sizes as they are often marketed (original shapes).

As depicted in FIG. 1, a patient who is prescribed numerous medication products is not infrequently confronted with a plurality and a variety of means for delivery of each such medication, including a tablet (1a), a large capsule (2a) and a gel cap (3a).

The present invention includes reformulating each of such medication products to minimize inactive ingredients, thus reducing the physical volume of each such means for delivery, and importantly shaping and configuring the physical outer appearance of each such medication product so that when inserted together with other such medication products into an outer container, which itself can be made from medication products, they each fit closely with those to which they are then contiguous.

FIG. 1 also depicts the medication products (1a), (2a) and (3a) in newly shaped and sized pill forms ("medication elements") depicted as (1b), (2b) and (3b), respectively.

The diameter of each said pill will often be the same, with that diameter having a minimum measurement consistent with the capabilities of pharmaceutical manufacturing equipment and a maximum measurement consistent with the swallowable size of a capsule of medication or use as a suppository into the appropriate orifice of a living body to which the particular medication is applicable.

Figure 2B:
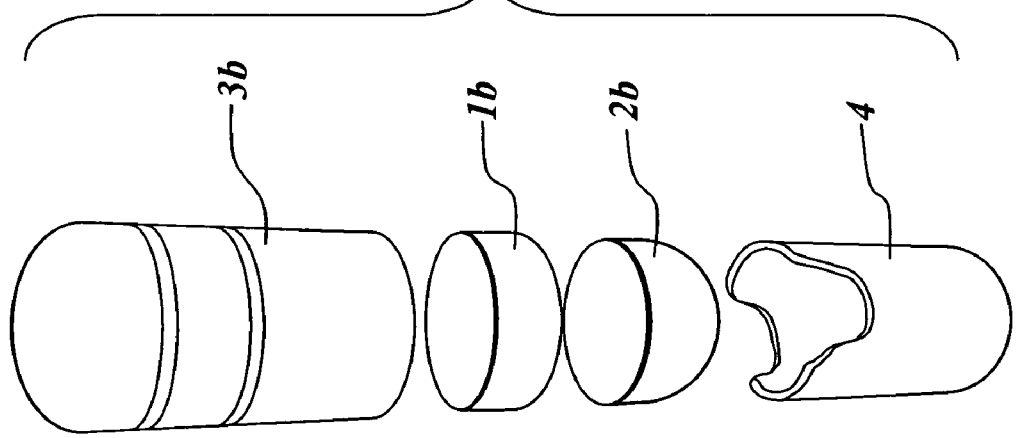
FIG. 2b is an expansion of the assembled medication delivery device of FIG. 2a, showing the individual components.
Figure 2A:
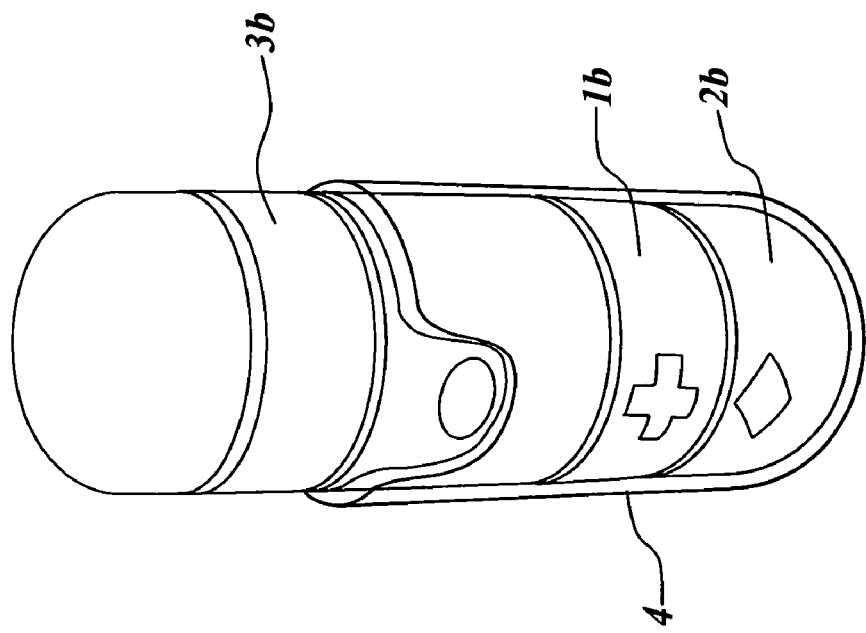
FIG. 2a is a depiction of assemblage of the new pills into a cup shaped outer container.

One embodiment of an outer container into which the shaped forms of the medications (1b), (2b) and (3b) are to be inserted is a cup shaped container ("outer containment means") (4) as depicted in FIGS. 2a and 2b, or a tube like container ("outer containment means") with narrowed orifices at both ends (8), as depicted in FIGS. 3a and 3b. These containers can be made of an inert or medically active biodegradable material.

As depicted in FIGS. 2a, 2b, 3a and 3b, the closure means by virtue of which pills, such as (1b) and (2b) which have been inserted into the outer containers (4) and (8), are retained therein is the use of a plug, preferably made as a soft gel capsule (3b).

In one embodiment, the medication readily contained in the plug (3b) is Omega 3 fish oil, or vitamins, or calcium/minerals, or other common dietary supplements or over-the-counter drugs, or a principal prescription medication. When the plug (3b) is in a soft gel form, it is readily suitable for containing liquid/oil medications.

The plug (3b) is inserted into the open end of the cup (4) or tube (8), thereby preventing the inadvertent discharge or spillage of pills (1b) and (2b) from the cup (4) or tube. The narrowed opposite opening of the tube (8) also serves to retain the pills.

As demonstrated in FIG. 3c, plug (3b) can be affixed to the cup (4) or tube (8) with a flexible inward pointing beak at part of the brim of the cup or tube and with one or more slits at the brim and reciprocal indentation system (undulations) at the surface of plug (3b), which is easily created if the plug is a soft gel or tablet. The flexible beak system also allows for maximal size of the inserts to pass into the container during the filling and trapping them inside the cup or the tube without needing to be physically attached to the container.

The plug can be released by either pushing upwards through the emerging pills at the opposite end of the tube or by pushing downwards through the partially removed brim.

Figure 4:
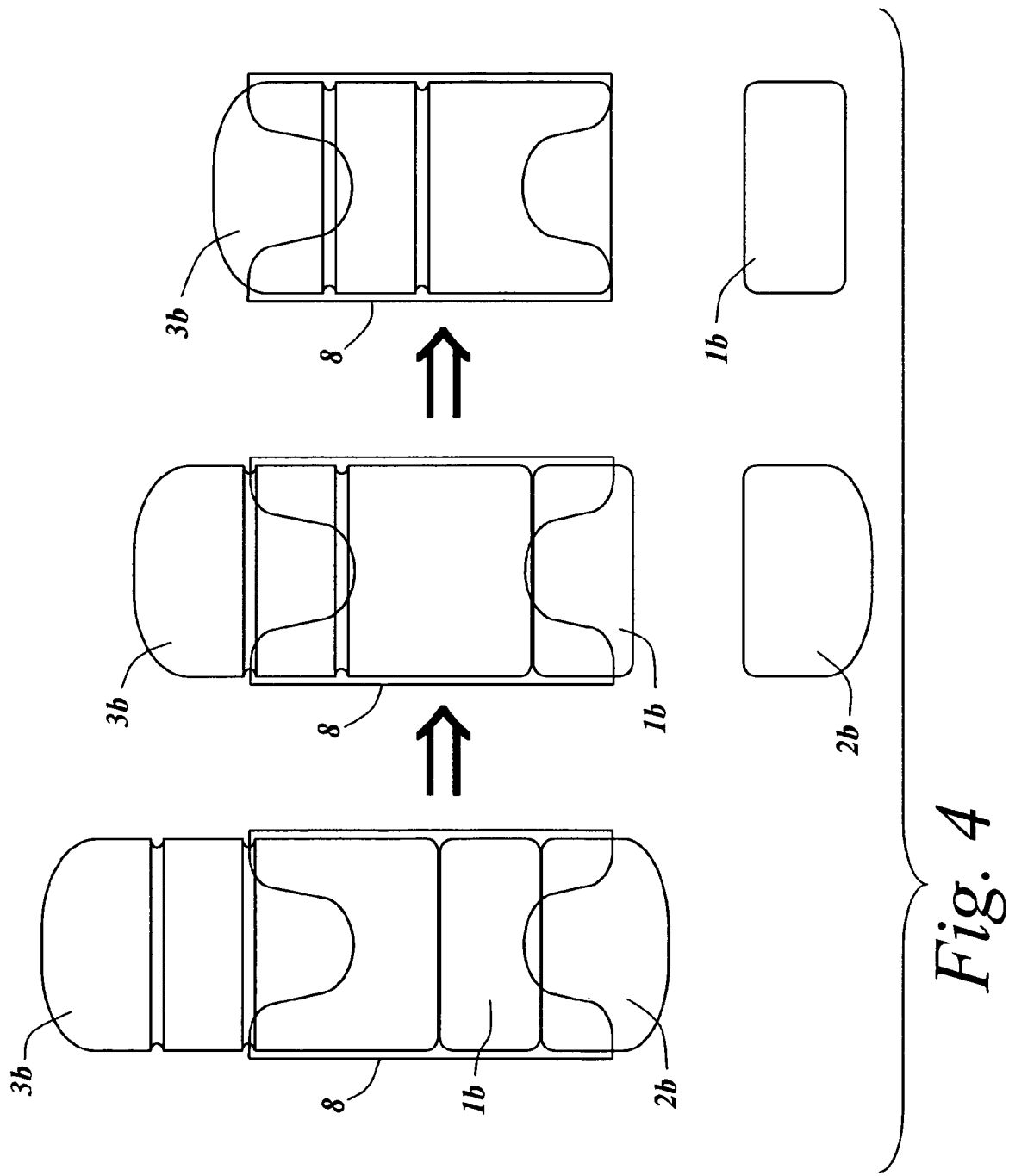
FIG. 4 is a depiction of expulsion of the pills from the outer tube-shaped container and also how the container can be volume adjustable or hold a variable number of pills.

Alternatively, the plug is not removed at all but serves as an expulsion means for the loose elements through the opposite opening of the tube (which also has the same flexible beaks as the plug opening) by being pushed and fully inserted into the tube (FIG. 4)

The use of pills (1b), (2b) and (3b) (rather than powders or granules) as the form of medication presentation avoids the irretrievable aspect associated with powders, in addition to the inability to assure proper dosage when powder medications are spilled.

In the event that the outer container, whether as depicted in FIG. 2 or in FIG. 3, or otherwise, is opened, whether inadvertently or intentionally, there is no risk of losing any amount of the active ingredient in the pill.

The present invention also includes multi medication delivery devices that are not volume-adjustable, but still allow for the combination of medication elements of differing types and sizes into one deliverable device, as depicted in FIGS. 5-12.

Figure 5:
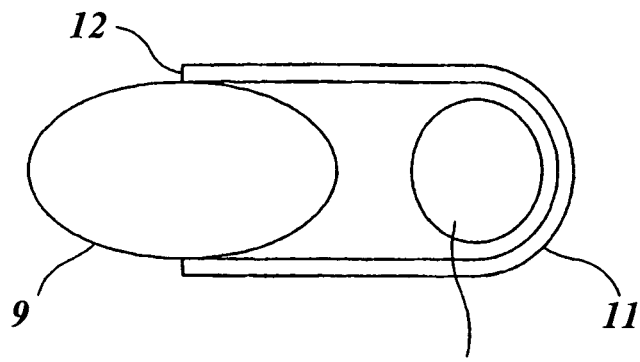
FIG. 5 is a depiction of a cup shaped outer container without any narrowing or split at the opening, holding a loose medication element (pill) and closed with a medication containing plug.

FIG. 5 is an embodiment of the invention in which one large pill (9) is assembled in association with a smaller pill (10), with said smaller pill inserted into a cup-shaped containment means (11), with said containment means then connected with and affixed to the larger pill at a connection area (12) by various means, including, but not limited to, a pressure fit between the outside surface of the larger pill in contact with the inner surface of the cup type device means.

Figure 6:
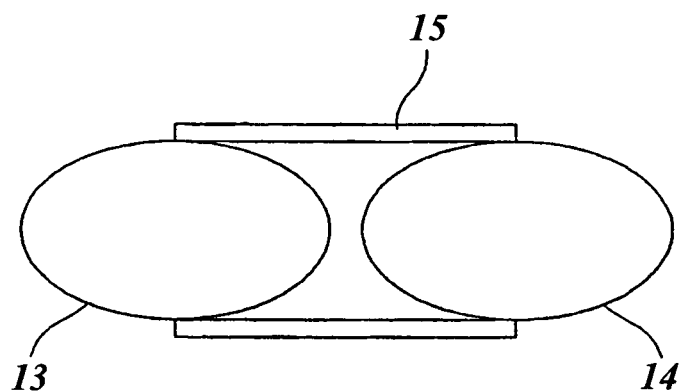
FIG. 6 is a cross section of yet another embodiment of the invention, depicting two separate compartments physically connected with each other.

FIG. 6 is another embodiment of the invention in which a first gel cap (13) is assembled in association with a second gel cap (14), with both of said gel caps being connected with and affixed to each other by means of a band of material (15) around the mid-section of each of the said gel caps.

Figure 7:
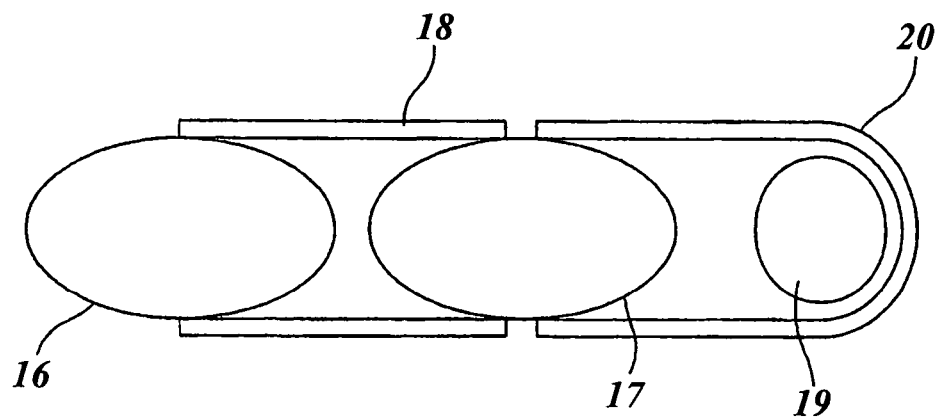
FIG. 7 is a depiction of a cup shaped outer container without any narrowing or split at the opening, holding a loose medication element (pill) and closed with a medication containing plug, with the medication containing plug physically connected to another medication element (pill).

FIG. 7 is a further embodiment of the invention in which a first pill (16) is assembled in association with and physically connected to a second pill (17) by means of a band of material (18) surrounding one-half of the said first pill (16) and one-half of the said second pill (17) which are in closest proximity to each other, as depicted in FIG. 6, with the said assemblage of the first pill and second pill then further assembled in association with a third pill (19), which said third pill is inserted or otherwise contained within a containment means (20), with said containment means then connected to pill (17) at a connection area by various means, including, but not limited to, a pressure fit between the outside surface of the second pill and the inner surfaces of containment means (20). In one embodiment, the band of material is attached to the medication elements through an adhesive, such as a glue or biodegradable glue. The adhesive can vary in hardness allowing for breakage or separation of the individual medication elements if desired.

Figure 8:
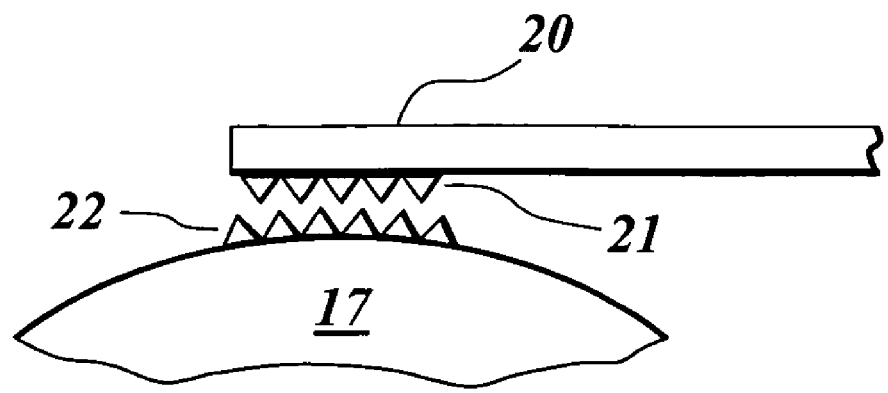
FIG. 8 is a depiction of a friction attachment system between the opening of the cup shaped container and the plug.

FIG. 8 is a variation of the devices in FIGS. 5 and 7, wherein the cup-shaped containment means is affixed to a pill by means of screw-type undulations (21) and (22), respectively. The undulations, or "teeth," allow the individual devices to be locked in place, which can be separated from each other only upon the exertion of substantial force. As demonstrated in FIG. 8, containment means (20) and pill (17) from FIG. 7 mate with each other as they are inserted into one another as a means of connecting them together.

Figure 9:
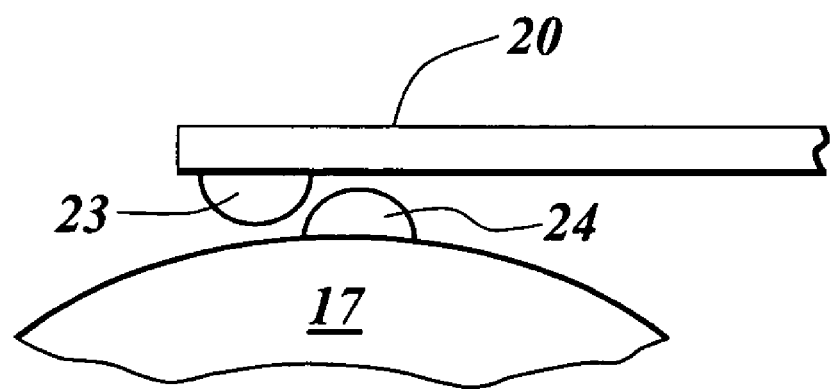
FIG. 9 is a depiction of a snap interlocking means between the opening of the cup shaped container and the plug.

FIG. 9 is another variation of the devices in FIGS. 5 and 7, wherein the containment means (20) and pill (17) are affixed to each other by means of an interlocking mechanism by way of nodules (23) and (24), in which respective nodules (23) and (24) are mechanically plastically deformable, thereby allowing and enabling the nodules to slide and slip over one another, resulting in the affixed assemblage of the containment means (20) and pill (17), which can be separated from each other only upon the exertion of substantial force applied to the pill and containment means simultaneously and in directions opposite to each other.

In an alternative embodiment of the invention, the medication elements are connected into a single delivery device in a chain, train or string fashion. Such a delivery device does not require an outer containment means. For example, FIG. 10 depicts one pill (25), two capsules of different sizes (26) and (27), and a gel cap (28), all of which contain varying medication products, and are of different sizes and shapes, that are stacked onto one another. In this instance, the particular order or sequence of such a connection is irrelevant.

In one embodiment, the individual elements are held together with an adhesive such as glue or biodegradable glue. The adhesive can vary in hardness allowing for breakage or separation of the individual medication elements if desired.

Additionally, the medication delivery device can be prepared by connecting individual medication elements of uniform dimensions in a chain, train or string fashion. For example, FIG. 11 shows a medication delivery device similar to the device of FIG. 10 but with individual medication elements (29), (30), (31) and (32) that do not vary in size. In this example, the individual elements are in oblong, rectilinear shapes. One advantage of this system is that elements with such dimensions allow for the maximum area of physical contact with one another. As with the device of FIG. 10, the particular order or sequence of such a connection is irrelevant, and the individual elements may be held together with an adhesive such as glue or biodegradable glue.

In another embodiment, individual medication elements can be placed in an inside (or "male") cup-shaped containment means, with a slightly larger outside (or "female") cup-shaped outer containment means placed around the inside containment means so as to enclose the individual medication elements within the inside containment means. An example of such an embodiment is shown in FIG. 12, wherein a number of medication elements of similar size and shape (33), (34), (35) and (36) are placed within the inside cup-shaped containment means (37), and an outside cup-shaped containment means (38) is placed over the inside cup-shaped containment means such that the medication elements are completely encapsulated. Both the inside and outside containment means can be made of transparent material so the user can examine the medication delivery devices within the containment means. Additionally, both the inside and outside containment means can be made of or contain active ingredients.

It should be noted that the medication delivery devices exemplified herein can be made with any number of individual medication elements. Additionally, the examples demonstrated in FIGS. 1-12 are not necessarily exhaustive of all embodiments of the invention.

Although the foregoing embodiments refer variously to tablets, soft gels, gel caps, capsules and casing, the invention is not limited to tablets, soft gels, gel caps and capsules as specifically shown and discussed herein, but rather encompasses any and all medication containers and containment means, including pills, gel caps and capsules.

In addition, although several of the preferred embodiments described herein are comprised, for illustration purposes, of a specific number of capsules, gel caps or pills, or combinations thereof, the invention is not limited to a specific number of capsules, pills and/or gel caps, but rather encompasses any number of containers or containment means.

This invention allows for a large variety of medication combinations, including solids and liquids, since they are all kept inside their own separate spaces/containers. The invention also permits incompatible substances like oils and water to be stored separately inside the same outer container, and is particularly suitable for soft gel and tablet combinations.

Typical medication combinations of inserts, plug and casing can include, for example:
1. Statins+omega 3+vitamins+aspirin+anti hypertension medication or any combinations thereof.
2. Anti-depressants/neuroleptics, including anti-convulsives, tranquilizers+omega 3+vitamins or other nutraceuticals or any combinations thereof.
3. NSAIDS/steroids/analgetics+nutraceuticals or any combinations thereof.
4. Metabolic medications+nutraceuticals.
5. Hormones+nutraceuticals.
6. Any medication combination the prescribing physician finds suitable for his or her patient.
7. Any medication combination suggested by medical authorities as part of chronic disease treatment or prevention.

This invention also allows for the containment of a variety of medication combinations using only two standard sized and shaped outer container elements (although more than two outer containment elements also may be used): the outer containment means (also referred to as the "casing") and the closure means (also referred to as the "plug"). By adjusting the position at which the plug is inserted within the casing, the internal volume and overall length of the device can be adjusted to the content size. For example, if the casing is 15 mm and the plug 17 mm, the total size can vary from 17 mm (15 mm of the plug occupying the total volume of the casing, with 2 mm of the plug extruding outside the casing), to about 24 mm (which is typically the maximum swallowable size for the average person, and is achieved when the plug is inserted 8 mm into the casing so that the casing constitutes 15 mm of the device and the extruding portion of the plug constitutes the remaining 9 mm of the device). The number of indentations on the surface or the surface structure of the plug can determine the number of possible positions or volume variations. Use of the invention as a rectal or vaginal suppository for animals or humans will allow for greater variations in the minimum and maximum allowable size.

It should be noted that the different volume positions of the medication delivery device are stable, and can only be adjusted by exerting a distinct force. In other words, normal handling of the device will not make the plug change from one position to another, nor will normal handling cause the plug to become separated from the casing.

By moving the plug into different positions within the casing, the total volume of the medication delivery device can be increased or reduced as necessary. The volume of the device can be increased to accommodate additional medication elements or decreased if medication elements are removed from the device. Additionally, the user can change the size of the device based not only on the number/size of the medication elements within the device (as is the case with, say, dividable tablets and multiple capsule medication delivery systems known in the prior art), but rather to accommodate personal size preferences. For example, one user may prefer to swallow larger pills, and therefore could adjust the volume of the medication delivery device containing 6 mm of medication elements to 24 mm in length. Another user may prefer to swallow smaller pills and could adjust the length of the same medication device containing 6 mm of medication elements to 10 mm in length.

Another important aspect of the medication delivery device is that the size of the device can be adjusted by both the manufacturer and the consumer. The volume or size change can easily be performed with the fingers of a typical user without any other necessary tools. The volume or size change also can be performed by machines. For example, if a nursing home, hospital or compound pharmacy has all of the individual components (e.g., casing, plug, inserts) they can prepare a medication delivery device for the individual patient by hand. The nursing home, hospital or compound pharmacy, for example, can manually prepare medication delivery devices for patients who can swallow a delivery device containing 5 medication elements, as well as smaller medication delivery devices containing 2 or 3 medication elements for other patients at the same location who can only swallow such smaller devices. Alternatively, a compound pharmacy having a medication delivery device filling machine can do the same as above, but mechanically.

Yet another important aspect of the volume adjustability associated with the medical device is that the end user can adjust the delivery device even as pre-prepared (e.g., as purchased or delivered from the compound pharmacy) according to need. For example, if a medication delivery device that was delivered to an individual is 24 mm in length and contains 4 medication elements, and the individual cannot manage to swallow this size, then the individual can remove 1 or 2 medication elements, swallow these separately and compress the delivery device to a smaller size by pushing the plug further into the casing.

It should also be noted that the integrity of the medical device is not destroyed, nor is its efficacy reduced, when the position of the plug is removed and then reinserted in the casing, or adjusted "up" and "down" so as to adjust the volume within the device.

From a manufacturing viewpoint the volume flexibility is important, since the plug can be at lowest degree of insertion at the filling and thus giving the machinery more leeway to precision, and the consumer can snap the plug into its most compact position at the time of use or expulse the content of the container, whichever is important to accommodate the swallowing abilities.

The active ingredients contained within each medication product are separated from the other active ingredients contained within the same said outer containment device by the physical properties of each medication product so coated, typically by coatings on tablets or by the shell of capsules or soft gels, thereby preventing the medication substance in one container compartment from mixing with the medication substance in the other container compartments. These coatings and shells can be colored according to a preset visual identification classification system related to disease systems (for example, different shades of red for the cardiovascular system). Each medication product (pill) can also carry a symmetrical symbol on the side of the pill as an additional identification means.

Consequently, there is no concern about the medication substances reacting with each other within the most outer container compartment, and the medication substances will therefore not represent a new chemical compound before being ingested or otherwise delivered into a live body.

The prospect of different medication substances actually being produced at locations distant from each other and then being consolidated in medication container devices in accordance with this invention makes this invention feasible, highly economically attractive and flexible. An additional benefit of this invention is that one step of traditional capsule filling is eliminated (that is, not needing any capsule top).

Creating a standardized volume variable container system that will meet the needs of a future automated individualized prescription fulfillment centers based on hosting interchangeable, standardized and visually recognizable medication elements, opens the door to a world wide, secure, personalized and comprehensive multi-medication manufacturing system.

The numerous advantages of this invention include:

(a) The ability to maintain the chemical stability of the different medication substances by preventing any chemical reaction between or among them by virtue of the fact that they are separated from each other by being in separate containers and compartments, thus making it possible, for example, to combine nutraceuticals with prescription drugs or several prescription drugs together;

(b) Ease of production of a means to deliver multiple medications simultaneously or sequentially, by virtue of each container compartment being capable of being produced and filled with different medications at remote distant locations, before the final assemblage using same manufacturing tools;

(c) Ease of assemblage since the container system uses an easy to fit plug;

(d) Facilitation of switching to less expensive generic medicines, since the active ingredients are inside one outer container the patient will not need to track the individual pills;

(e) Flexibility of combination or dosage, since the content or concentration can be changed for one substance without influencing the chemical properties of the other;

(f) Physician control, since the outer container can easily be opened by the patient by the release system, the physician can remove or add individual active ingredients if desired;

(g) Increased drug therapy power as more patients will accept taking synergistic drug combinations as long as the total number of pills remain low;

(h) Increased patient compliance and assurance that the patient is actually taking several medical substances since they come as "one dose";

(i) Increased patient compliance because the patient will be more willing to take one pill compared to several, or even if the patient has to open the outer container and take each active ingredient sequentially, the invention still reduces the number of pill boxes and keeps the medication in one place;

(j) Reducing the risk of medication confusion both for the patient and/or the staff at for example nursing homes, hospitals, since there will be fewer pills to keep track of;

(k) Providing a precise "medical" communication, because it shows clearly which products are combined (not mixed) and they can be visualized and identified through the "see through" outer container by color and symbols;

(l) Ease of fulfillment, as the plugs and inserts can be made symmetrical for the ease of filling the containers as it will not matter whether the pills come up side down through the feeding tubes. This also applies to the use of symmetrical symbols on the side of the pills. A symmetrical symbol is for example a circle, cross, square, horizontal or vertical lines. Such symbols should also be readily recognized by technical means for the purpose of identification of the pill;

(m) Means for always maintaining smallest (and most patient friendly) overall volume by having an adjustable volume device that will adapt to the medication content;

(n) Increase in safety against terrorism/fraud of content, since the manufacturing will require specific tools and components and the appearance will be striking and the content easily recognizable.

Additionally, embodiments of the invention where the medication delivery device is of a fixed volume represent other attractive alternatives to traditional medications. For example, a more permanently fixed attachment system encasing the individual medication elements within the containment means may offer enhanced mechanical stability. A fixed-volume medication delivery device allows for the manufacture of specific and solid dose medication combinations where the user can decide to either consume or not consume the whole unit, as would be in the case for a combination of individual nutraceuticals and/or over-the-counter medications. Moreover, the fixed-volume medication devices, which contain no plug, have smooth outer surfaces, which, for some users, may be easier to swallow. Additionally, simply gluing the medication elements together removes any size limitations that may be imposed by an outer containment means. Medication elements that are attached in a chain, train or string fashion that may be too large for a user to swallow can also be broken into devices of smaller sizes for easier ingestion.

Furthermore, by standardizing the diameter and the shape of the different medication products as described herein, it becomes possible to thereby obtain an optimal physical configuration that favors the swallowing reflex and also reduces the "dead" space to a minimum, thus making the total volume of the medicinal delivery device as small and as compacted as possible and holding as many active ingredients inside as possible.

In addition, by standardizing the diameter and the shapes of the different containers, it becomes possible to customize the medicinal product delivery device to the individual patient. The ability to interchange the same shape and adjusted size components allows for the manufacturing of different variation of inner component medications. The dosages can also be individualized by repeating one medication container in order to get, for example, a double dose.

Also, by standardizing the diameter and the shape of the different containers, the invention allows for putting many medications into "one" pill, rather than using several.

Another advantage of the invention is that by standardizing the diameter and the shape of the different containers, it becomes possible to build standardized automated feeding machines for an assembly line. The medical prescription coming from a physician can then be translated into the invented delivery system, adjusted to the patient's weight, sex, and age, simply by using multiple inner container feeders, each holding different medications. Such a process presents a means for creating a new international industry, consisting of combined assembly line/fulfillment centers/pharmacies that can communicate directly with the physicians or prescription centers all over the world, to produce these individualized multi medication devices based upon a single digital classification system merely referring to for example color, ingredient and doses or a reference number.

The invention claimed is:

1. A digestible, reversible, and volume-adjustable device for the delivery of multiple medications to a subject, the device comprising:
    multiple medication elements;
    an outer containment means having at least one open end into which the medication elements are removeably inserted; and
    a closure means removeably and adjustably inserted into at least one end of the outer containment means;
    wherein at least one end of the outer containment means comprises a narrowed orifice with a flexible edge that contacts the closure means; and
    wherein the medication elements are selected from the group consisting of a tablet, a capsule, a gel capsule, a soft gel capsule, and combinations thereof.

2. The volume-adjustable device of claim 1, wherein the closure means is itself a medication element.

3. The volume-adjustable device of claim 2, wherein the medication element comprises a soft-gel capsule.

4. The volume-adjustable device of claim 3, wherein the soft-gel capsule contains omega-3 fish oil, multivitamins, minerals, nutraceuticals, over-the-counter medications, prescription medications or inert materials.

5. The volume-adjustable device of claim 1, wherein the outer container means comprises a hollow tube wherein both ends of the tube are open such that the medication elements or closure means can be removeably inserted or expelled through the ends.

6. The volume-adjustable device of claim 1, wherein the outer container means comprises a hollow tube wherein one end of the tube is open so that the medication elements or closure means can be removeably inserted or expelled through the open end, and the other end is closed so that the medication elements or closure means, once inserted, can not be expelled through the closed end.

7. The volume-adjustable device of claim 1, wherein at least one open end of the outer containment means has a slit to provide flexibility to the edge of the open end, such that the medication elements or closure means can easily fit through the opening.

8. The volume-adjustable medication device of claim 1, wherein the outer-containment means is made of a transparent material.

9. The volume-adjustable medication device of claim 1, wherein the outer-containment means is made of a biodegradable material.

10. The volume-adjustable medication device of claim 1, wherein the outer-containment means is made of a material formulated with a medication product.

11. The volume adjustable device of claim 1, wherein the medication elements contain a nutraceutical or pharmaceutical product.

12. The volume-adjustable medication device of claim 1, wherein the medication elements are colored differently according to their content.

13. The volume-adjustable medication device of claim 1, wherein the medication elements have distinct symbols on their sides.

14. The volume-adjustable medication device of claim 1, wherein the medication elements have a non-circular horizontal surface that allows the medication product to be lined up in such a way the distinct symbols are arranged in linear fashion.

15. The volume-adjustable medication device of claim 1, wherein the closure means has an undulating surface with a number of indentations that the edge of the narrowed orifice of the outer containment means can insert into, such that the medication device has a variable volume depending on the position of the closure means in order to hold medication elements of varying shapes and sizes.

16. The volume-adjustable medication device of claim 1, wherein the medication elements have a uniform diameter.

17. The volume-adjustable medication device of claim 1, wherein the medication elements comprise, respectively, at least one tablet and at least one capsule or soft gel.

18. The volume-adjustable medication device of claim 1 further comprising a second outer containment means containing one or more medication elements, the second outer containment means being affixed to the first outer containment means.

19. The volume-adjustable medication device of claim 18, wherein the second outer containment means is affixed to the first outer containment means by a common closure means, the common closure means being partly inserted into the at least one open end of each of the first and second outer containment means.

20. The volume-adjustable medication device of claim 19, wherein the common closure means is comprises a medication element.

21. A digestible, reversible, and volume-adjustable device for the delivery of multiple medications to a subject, the device comprising:
    multiple medication elements;
    an inner containment means having at least one open end into which the medication elements are removeably inserted;
    an outer containment means having at least one open end into which the inner containment means is removeably and adjustably inserted, such that the medication elements are completely encapsulated;
    wherein at least one end of the outer containment means comprises a narrowed orifice with a flexible edge that contacts the inner containment means; and wherein the medication elements are selected from the group consisting of a tablet, a capsule, a gel capsule, a soft gel capsule, and combinations thereof.

22. The volume-adjustable medication device of claim 21, wherein the outer and inner containment means are made of transparent material.

23. The volume-adjustable medication device of claim 21 wherein the outer and inner containment means are made of a biodegradable material.

24. The volume-adjustable medication device of claim 21, wherein the outer and inner containment means are made of a material formulated with a medication product.

25. The volume adjustable device of claim 21 wherein the medication elements contain a nutraceutical or a pharmaceutical product.

26. The volume-adjustable medication device of claim 21 wherein the medication elements are colored differently according to their content.

27. The volume-adjustable medication device of claim 21, wherein the medication elements have a uniform diameter.

* * * * *